United States Patent [19]
Mori et al.

[11] Patent Number: 5,776,488
[45] Date of Patent: Jul. 7, 1998

[54] LIPOSOME PREPARATION

[75] Inventors: Yoshiyuki Mori; Kazuyoshi Sagara; Hiroaki Mizuta, all of Chikujo-gun; Akihiro Fujii, Iruma, all of Japan

[73] Assignee: Yoshitomi Pharmaceutical Industries, Ltd., Osaka, Japan

[21] Appl. No.: 716,201

[22] PCT Filed: Mar. 8, 1995

[86] PCT No.: PCT/JP95/00383
§ 371 Date: Sep. 10, 1996
§ 102(e) Date: Sep. 10, 1996

[87] PCT Pub. No.: WO95/24201
PCT Pub. Date: Sep. 14, 1995

[30] Foreign Application Priority Data

Mar. 11, 1994 [JP] Japan .................... 6-041065

[51] Int. Cl.[6] .................... A61K 9/127; A61K 9/133
[52] U.S. Cl. .................... 424/450
[58] Field of Search .................... 424/450

[56] References Cited

U.S. PATENT DOCUMENTS 5,246,708  9/1993  Borstel .................... 424/450

OTHER PUBLICATIONS

Allen et al., Biochemica et Biophysica Acta., vol. 643 (1981), pp. 346–362.

Kobayashi, Kobunshi (1980) vol. 29 (2), p. 117.

Kataoka et al., Annals New York Academy of sciences (1978) vol. 308, pp. 387–394.

Rustum et al., Cancer Research, vol. 39(4), pp. 1390–1395 (1979).

Kobayashi et al., Int. J. Cancer, vol. 20, pp. 581–587 (1977).

*Primary Examiner*—Gollamudi S. Kishore
*Attorney, Agent, or Firm*—Wenderoth, Lind & Ponack

[57] ABSTRACT

A liposome preparation comprising a water-soluble 2'-deoxy-2'methylidenecytidine compound encapsulated therein and a compound which positively charges the surface of lipid membrane. This liposome preparation is not only expected to decrease toxicity to myeloid tissue, which is caused by a water-soluble 2'-deoxycytidine compound having anti-malignant tumor activity, but also expected to accumulate the active ingredient in tumor tissues by virtue of an improved residence thereof in blood. Therefore, the preparation can maintain or enhance anti-tumor effects without causing side effects, and is useful for the treatment of malignant tumors.

13 Claims, 5 Drawing Sheets

Time after initiation of treatment

LIPOSOME PREPARATION

This application is a 371 of PCT/J895/00383 filed Mar. 8, 1995.

1. Technical Field

The present invention relates to a liposome preparation which suppresses migration, to bone marrow, of a water-soluble 2'-deoxycytidine compound having an anti-malignant tumor activity, and which enhances migration thereof to tumor tissues.

2Background Art

Of the therapies of malignant tumors, chemical treatment is among the effective treatments along with surgical treatment and radiation treatment. However, an anti-malignant tumor agent which selectively eradicates tumor tissue cells has not been developed to date, and reduction of side effects such as myelotoxicity has been the problem to be solved during use. An attempt has been made to reduce side effects and enhance antitumor effects by modification, by pharmaceutical methods, of an anti-malignant tumor agent into a targeted preparation which targets malignant tumor tissues. Clinical tests have proved superior anti-malignant tumor effects achieved by a local administration of an anti-malignant tumor agent containing neocarzinostatin combined with a styrene-maleic acid anhydride copolymer, which have been suspended in an oily contrast medium, to malignant tumor tissue sites in the liver for the treatment of the malignant tumor by virtue of accumulation of the preparation thereof in the malignant tumor tissue [Cancer Research, vol 44, pp. 2115–2121 (1984)]. However, this method is associated with difficulties in that a special administration skill is needed and the number of applicable malignant tumors is limited. A method has been sought, therefore, which enables reduction of side effects and enhancement of anti-malignant tumor effects by systemic administration.

Of such studies, a method comprising encapsulating an anti-malignant tumor agent in liposomes has been known, which utilizes the tendency, when compared to normal tissues, of malignant tumor tissues toward easy uptake of microparticles, such as liposomes, which are fine and closed vesicles having a lipid bilayer structure formed upon dispersion of phospholipids or glycolipids in aqueous solutions. Encapsulation of an anti-malignant tumor agent in liposomes has revealed high anti-malignant tumor effects resulting from the suppression of adverse influences on normal cells and possible consecutive administration of the agent in large doses. Yet, mere formulation into liposomes does not suppress migration of an anti-malignant tumor agent to myeloid tissues, nor does it allow sufficient accumulation of the agent in malignant tumor tissues. Thus, an attempt has been made to prolong residence of the agent in blood by various modifications of liposomes, whereby to ultimately accumulate the anti-malignant tumor agent in malignant tumor tissues. Such attempt includes (1) decreasing the particle size of liposomes [Cancer Research, vol 36, pp. 2949–2957 (1976)], (2) using a liposome membrane structure-reinforcing factor such as phosphatidylcholine having long chain saturated fatty acid [Biochimica et Biophysica Acta, vol. 839, pp. 1–8 (1985)], (3) adding a synthetic lipid of a water-soluble polymer (e.g., polyethylene glycol), a natural polysaccharide or a sugar which has been bound with fatty acid, cholesterol, etc. [Biochimica et Biophysica Acta, vol. 1113, pp. 171–199 (1992), and Oyo Saibo Seibutsugaku Kenkyu, vol. 9 (3–4), pp. 53–61 (1992)] and other methods, and the third method in fact has achieved accumulation in malignant tumor tissues. However, no report has documented a successful suppression of migration of an anti-malignant tumor agent to myeloid tissues, the site of expression of side effects caused by the anti-malignant tumor agent, and the problem regarding the expression of myelotoxicity has not been resolved.

In the meantime, it has been reported that migration to myeloid tissues was enhanced by applying a negative charge to the membrane surface of liposomes [Biochimica et Biophysica Acta, vol. 401, pp. 336–348 (1975)]. This literature only reports incorporation of ethylenediaminetetraacetic acid into myeloid tissues. Although application of positive charge to the membrane surface of liposomes has been known, there are only reports of a liposome preparation aiming at increasing the concentration of calcium in serum (Japanese Patent Application under PCT laid-open under Kohyo No. 500378/1988), a liposome preparation aiming at supply of magnesium to patients with traumatic encephalopathy (WO 88/07852), a liposome preparation directed to the suppression of liberation of an active ingredient prostaglandin (Japanese Patent Unexamined Publication No. 95118/1991), a liposome preparation having a high drug encapsulation ratio, which is obtained by adding, to a lyophilized liposome preparation charged positive or negative, an aqueous solution of a drug, which has been charged conversely from the liposome preparation (Japanese Patent Unexamined Publication No. 103527/1992), a liposome preparation useful for the treatment of ophthalmic diseases and having an external lipid layer containing a specific ingredient, which is designed to increase binding to mucosal tissues (Japanese Patent Application under PCT laid-open under Kohyo No. 500360/1990), a mucin-targeted liposome preparation having affinity for mucin membrane of warm-blooded animal, wherein the surface region thereof assumes positive charge by the use of two kinds of bipolar lipid molecules each having a specific structure (Japanese Patent Application under PCT laid-open under Kohyo No. 503408/1991), a liposome preparation containing a specific compound having excess positive charge, which is suitable as a drug carrier preparation for treating liver diseases for its liver-specific behavior (Japanese Patent Unexamined Publication No. 506661/1993), an insulin liposome preparation for oral administration [Endocrinol. Jpn., vol. 26, pp. 337–344 (1979)] and a liposome preparation containing ciclosporin A [Journal of Microencapsulation, vol. 6, pp. 117–182 (1989)].

Meanwhile, U.S. Pat. No. 5,183,882 discloses an injectable composition having superior stability during preservation, which contains 2'-deoxy-2'-methylidenecytidine dihydrate and sugars.

DISCLOSURE OF THE INVENTION

The present invention aims at providing a preparation which suppresses myelic migration of a water-soluble 2'-deoxycytidine compound having an anti-malignant tumor activity and prolongs residence thereof in blood, whereby to consequently improve migration to malignant tumor tissues.

The present inventors have conducted intensive studies for the purpose of solving the above-mentioned problems, and found that a liposome preparation can be prepared, which suppresses myelic migration of an active ingredient and prolongs residence thereof in blood, whereby to consequently enhance migration to malignant tumor tissues, by encapsulating a 2'-deoxycytidine compound in liposomes and charging the membrane surface of the liposome preparation positive, which resulted in the completion of the invention. Accordingly, the present invention relates to a liposome preparation comprising a water-soluble 2'-deoxycytidine compound encapsulated therein and a compound which positively charges the surface of a lipid membrane.

DETAILED DESCRIPTION OF THE INVENTION

As mentioned earlier, the liposome to be used for the liposome preparation of the present invention is a closed vesicle having internal aqueous phase portion enclosed by a lipid bilayer membrane formed by dispersing a phospholipid (lecithin) constituting the cell membrane in water, and grouped into three kinds of Multilamellar Vesicle (MLV), Large Unilamellar Vesicle (LUV) and Small Unilamellar Vesicle (SUV) according to the size and number of lipid bimolecules. Any kind of liposomes can be used in the present invention. The liposome preparation of the present invention should form a stable liposome structure in living organisms. When the movement of lipid bilayer membrane constituting the liposome becomes intense due to temperature, there occur drastic changes in membrane volume, membrane thickness, fluidity and membrane permeability after exceeding a phase transition temperature, which may possibly lead to eluting out of the encapsulated drug. To prevent this, the liposome needs to be prepared from a phospholipid having a gel-liquid phase transition temperature of not less than 37° C. Examples of such phospholipid include those having a preferable gel-liquid phase transition temperature of 40°–65°, such as hydrogenated purified egg yolk phosphatidylcholine (phase transition temperature 50°–60° C., hereinafter to be referred to as HEPC), hydrogenated purified soy bean phosphatidylcholine (phase transition temperature 55° C., hereinafter to be referred to as HSPC), dipalmitoylphosphatidylcholine (phase transition temperature 42° C., hereinafter to be referred to as DPPC) and distearoylphosphatidylcholine (phase transition temperature 55° C., hereinafter to be referred to as DSPC), with preference given to HSPC and DPPC. These may be used alone or in combination. The liposome usable in the present invention is prepared from these phospholipids, preferably combined with sterols which reportedly improve stability of liposome in the living body, such as cholesterol [Biochemm. J., 186, pp. 591–598 (1980)] and cholestanol, or a stabilizer such as sphingomyelin.

The 2'-deoxycytidine compound which is the active ingredient to be used in the present invention is water soluble and can be included in the inner phase of liposomes. The 2'-deoxycytidine compound is selected from 2'-deoxy-2'-methylidenecytidine (Japanese Patent Unexamined Publication No. 258818/1988), 2'-deoxy-2'-fluoromethylidenecytidine [Journal of American Chemical Society, vol. 113, pp. 7439–7440 (1991)], 2'-deoxy-2'-methylidene-5-fluorocytidine (Japanese Patent Unexamined Publication No. 138292/1990), 2'-deoxy-2',2'-difluorocytidine (Japanese Patent Unexamined Publication No. 148193/1986), 2'-C-cyano-2'-deoxy-β-arabinofranosylcytosine (Japanese Patent Unexamined Publication No. 235182/1992), pharmaceutically acceptable salts thereof and hydrates thereof. Preferred are 2'-deoxy-2'-methylidenecytidine, 2'-deoxy-2'methylidene-5-fluorocytidine, pharmaceutically acceptable salts thereof and hydrates thereof, and particularly preferred is 2'-deoxy-2'-methylidenecytidine dihydrate (Japanese Patent Unexamined Publication No. 240794/1991, hereinafter to be referred to as DMDC).

The liposome preparation of the present invention is characterized in that the surface of the lipid membrane is positively charged, and the compound to positively charge the lipid membrane, namely, the surface of liposome, is selected from saturated or unsaturated aliphatic amines (e.g., stearylamine and oleylamine), sphingosine, phosphatidylethanolamine, N-[1-(2,3-dioleyloxy)propyl]N, N,N-trimethylammonium chloride, cholesterylhemisuccinate, 3B-[N-(N',N'-dimethylaminoethane)carbamoyl]cholesterol and cholesteryl(4'-trimethylammonio)butanoate, with preference given to stearylamine and sphingosine.

The liposome preparation of the present invention contains a compound capable of positively charging the surface of the lipid membrane in a proportion of 0.001–0.4 mole, preferably 0.02–0.4 mole, and a stabilizer in a proportion of 0.6–1 mole per mole of phospholipid.

The liposome preparation of the present invention can be prepared by a method known per se. For example, conventionally used hydration, reversed phase evaporation, removal of surfactant, solvent injection, freeze-thawing and dehydration-rehydration may be employed. In the hydration method, a phospholipid and a compound which positively charges the surface of lipid membrane are dissolved in an organic solvent (e.g., chloroform and ether) which does not denature them, and the solvent is evaporated from the resulting solution to give a thin lipid membrane. A solution containing a water-soluble 2'-deoxycytidine compound is added to the obtained thin membrane, and the mixture is subjected to agitation and sonication to give a liposome preparation encapsulating the water-soluble 2'-deoxycytidine compound. The solvent of the solution containing a water-soluble 2'-deoxycytidine compound may be any as long as it can be set for a temperature about 10° C. higher than the gel-liquid phase transition temperature, does not denature or decompose liposomes, and is physiologically acceptable, such as water, physiological saline and buffer.

In the reversed-phase evaporation, a phospholipid and a compound which positively charges the surface of lipid membrane are dissolved in an organic solvent (e.g., chloroform and ether) which does not denature them, and a solution containing a water-soluble 2'-deoxycytidine compound is added to the obtained solution. The obtained mixture is subjected to agitation, sonication and high pressure homogenation to uniformly disperse the water-soluble 2'-deoxycytidine compound. The solvent is evaporated from this dispersion to give a liposome preparation encapsulating the water-soluble 2'-deoxycytidine compound. The solvent of the solution containing a water-soluble 2'-deoxycytidine compound may be any as long as it does not denature or decompose liposomes and is physiologically acceptable, such as water, physiological saline and buffer.

In the removal of surfactant, a phospholipid and a compound which positively charges the surface of lipid membrane are mixed with a surfactant (e.g., cationic surfactant such as cholic acid and deoxycholic acid, and non-ionic surfactant such as Triton X-100 and octyl-D-glucoside) and a solution containing a water-soluble 2'-deoxycytidine compound, which is followed by agitation, sonication and high pressure homogenation to uniformly disperse the water-soluble 2'-deoxycytidine compound. The surfactant is removed from this dispersion to give a liposome preparation encapsulating the water-soluble 2'-deoxycytidine compound. The solvent of the solution containing a water-soluble 2'-deoxycytidine compound may be any as long as it does not denature or decompose liposomes and is physiologically acceptable, such as water, physiological saline and buffer. The surfactant can be removed by dialysis, gel filtration and ultrafiltration, which are applied singly or in combination.

In the solvent injection, a phospholipid and a compound which positively charges the surface of lipid membrane are dissolved in an organic solvent (e.g., ether and dichlorofluoromethane) which does not denature them, and the resulting solution is added to a solution containing a water-soluble 2'-deoxycytidine compound, which has been set for a temperature about 10° C. higher than the boiling point of the organic solvent. Then, the organic solvent is evaporated to give a liposome preparation encapsulating the water-soluble 2'-deoxycytidine compound. The solvent of the solution containing a water-soluble 2'-deoxycytidine compound may be any as long as it does not denature or decompose liposome and is physiologically acceptable, such as water, physiological saline and buffer.

In the freeze-thawing, liposomes prepared by subjecting a phospholipid and a compound which positively charges the surface of lipid membrane to a method known per se, such as hydration, reversed phase evaporation, removal of surfactant, injection of solvent, freeze-thawing and dehydration-rehydration, are subjected to sonication and high pressure homogenation to give small unilamellar vesicles (SUV). The SUV and a solution containing a water-soluble 2'-deoxycytidine compound are frozen with a cooling medium such as liquid nitrogen, and thawed at a temperature about 10° C. higher than the gel-liquid phase transition temperature to give a liposome preparation encapsulating the water-soluble 2'-deoxycytidine compound. The solvent of the solution containing a water-soluble 2'-deoxycytidine compound may be any as long as it does not denature or decompose liposomes and is physiologically acceptable, such as water, physiological saline and buffer.

In the dehydration-rehydration, a phospholipid and a compound which positively charges the surface of lipid membrane are dissolved in a water-miscible solvent (e.g., ethanol) which does not denature them, and the resulting solution is added to an aqueous layer being stirred. Preferably, the resulting mixture is subjected to high pressure homogenation and sonication to give small unilamellar vesicles (SUV). An isotonizing agent such as sugars and polyhydric alcohols (e.g., monosaccharides such as glucose and lactose, disaccharides and glycerol and propylene glycol) is added to the aqueous layer, and the mixture is set to have a temperature about 10° C. higher than the gel-liquid phase transition temperature of the phospholipid. The SUV can be also obtained by subjecting the liposome prepared by a method known per se, such as hydration, reversed phase evaporation, removal of surfactant, freeze-thawing and dehydration-rehydration, to sonication and high pressure homogenation. A solution containing a water-soluble 2'-deoxycytidine compound is added to this SUV suspension, and the mixture is frozen and dried under reduced pressure (about 0.1-about 0.2 mmHg) to give a freeze-dried product. The solvent of the solution containing a water-soluble 2'-deoxycytidine compound may be any as long as it does not denature or decompose liposomes and is physiologically acceptable, such as water, physiological saline and buffer. A dispersion solvent is added to the freeze-dried liposomes and the mixture is vigorously stirred in a vortex mixer to give a liposome preparation encapsulating the water-soluble 2'-deoxycytidine compound. The dispersion solvent may be the same as the above-mentioned solvent for the solution containing a water-soluble 2'-deoxycytidine compound which is set for a temperature about 10° C. higher than the gel-liquid phase transition temperature.

In the present invention, a sizing treatment is preferably applied to make the particle size of the drug-encapsulating liposomes more uniform. For example, an apparatus (Extruder, manufactured by Lipex Biomembranes Inc.) set for a temperature about 10° C. higher than the gel-liquid phase transition temperature of the lipid is used and the liposomes are forcibly passed through the same membrane filter having a certain pore size several times. The same step is repeated using membrane filters having larger pore sizes which are successively changed to the filters having smaller pore sizes to adjust the average particle size to about 50 to 200 nm, preferably 100–180 nm, more preferably 120–160 nm and particularly preferably 150–160 nm.

By the above process, the liposome preparation of the present invention is prepared, which is subjected to one or more treatments as necessary from ultracentrifugation, molecular sieve treatment, gel filtration, ultrafiltration and dialysis, so that a water-soluble 2'-deoxycytidine compound which was not encapsulated in liposome is removed.

The liposome preparation of the present invention can be prepared into an aqueous suspension together with a stabilizer [e.g., ascorbic acid, α-tocopherol and 3,5-di-tert-butyl-4-hydroxytoluene (BHT)], an isotonizing agent (e.g., glycerol, glucose and sucrose) and the like, or into a lyophilized preparation by freeze-drying, with preference given to a lyophilized preparation which is used as an injection (intravenous, intramuscular or subcutaneous preparation) after suspending in or diluting with a physiologically acceptable aqueous solution when in use. These preparations may be designed such that an effective amount thereof can be used for the treatment of malignant tumors [e.g., lung cancer, gastrointestinal cancer (e.g., esophageal cancer, stomach cancer, colic cancer, cancer of rectum and colon cancer), breast cancer, cancers in the neck, gynecological cancers (e.g., uterus cancer, cervical cancer and ovary cancer), urinary cancer (e.g., renal cancer and bladder cancer), leukemia, melanoma, and lymphogenous metastatic tumor] in mammals such as human. Such preparation is, for example, administered as an intravenous injection containing 1–500 mg of a water-soluble 2'-deoxycytidine compound, which is administered once a day or in doses which may be increased or decreased as appropriate.

The present invention is explained in more detail in the following by Examples and Experimental Examples.

EXAMPLE 1

DPPC (220.2 mg), cholesterol (69.0 mg) and stearylamine (32.4 mg) in DPPC:cholesterol:stearylamine=50:30:20 mol % were dissolved in 10 ml of ethanol heated to about 60° C., and this ethanol solution was poured into a 5 wt % aqueous glucose solution (200 ml) being stirred with heating at about 55° C. to give a suspension of liposomes having a small particle size of about 60 nm. This liposome suspension was subjected to ultrafiltration to remove ethanol, and concentrated to about 10 ml. A 1.5 wt % aqueous DMDC solution (10 ml) was added to this liposome suspension and the mixture was freeze-dried. Purified water (10 ml) heated to about 55° C. was added to this freeze-dried liposome product. After rehydration, a stirring treatment gave a liposome suspension. To unify the liposome particle size of this suspension, the suspension was subjected to a sizing treatment using an Extruder (manufactured by Lipex Biomembranes Inc.) equipped with a Nucleopore membrane (manufactured by Nomura Microscience) having a pore diameter of from 0.6 to 0.2 µm to give liposomes having a uniform average particle size of about 160 nm. Then, DMDC not encapsulated was removed by ultrafiltration to give DMDC liposomes.

EXAMPLE 2

HSPC (235.5 mg), cholesterol (69.6 mg) and stearylamine (32.4 mg) in HSPC:cholesterol:stearylamine=50:30:20 mol % were dissolved in 10 ml of warm ethanol heated to about 60° C, and this ethanol solution was poured into a 5 wt % aqueous glucose solution (200 ml) being stirred with heating at about 70° C. to give a suspension of liposomes having a small particle size of about 60 nm. This liposome suspension was subjected to ultrafiltration to remove ethanol, and concentrated to about 10 ml. A 1.5 wt % aqueous DMDC solution (10 ml) was added to this liposome suspension and the mixture was freeze-dried by a conventional method. Purified water (10 ml) heated to about 70° C. was added to this freeze-dried liposome product. After rehydration, a stirring treatment gave a liposome suspension. To unify the liposome particle size of this suspension, the suspension was subjected to sizing treatment using an Extruder (manufactured by Lipex Biomembranes Inc.) equipped with a Nucleopore membrane (manufactured by Nomura Microscience) having a pore diameter of from 0.6 to 0.2 µm to give uniform liposomes having an average particle size of about 160 nm. Then, DMDC not encapsulated was removed by ultrafiltration to give DMDC liposomes.

EXAMPLE 3

HSPC (392.5 mg), cholesterol (174.0 mg) and stearylamine (13.5 mg) in HSPC:cholesterol:stearylamine= 50:45:5 mol % were dissolved in 20 ml of warm ethanol heated to about 60° C., and this ethanol solution was poured into distilled water (400 ml) for injection being stirred with heating at about 70° C. to give a suspension of liposomes having a small particle size of about 60 nm. This liposome suspension was subjected to ultrafiltration to remove ethanol, and concentrated to about 30 ml. DMDC (150 mg) was added to this liposome suspension and the mixture was freeze-dried by a conventional method. A 5 wt % aqueous glucose solution (10 ml) heated to about 70° C. was added to this freeze-dried liposome product. After rehydration, a stirring treatment gave a liposome suspension. To unify the liposome particle size of this suspension, the suspension was subjected to sizing treatment using an Extruder (manufactured by Lipex Biomembranes Inc.) equipped with a Nucleopore membrane (manufactured by Nomura Microscience) having a pore diameter of from 0.6 to 0.2 µm to give uniform liposomes having an average particle size of about 160 nm. Then, DMDC not encapsulated was removed by ultrafiltration to give DMDC liposomes.

EXAMPLE 4

HSPC (392.5 mg), cholesterol (174.0 mg) and sphingosine (15.0 mg) in HSPC:cholesterol:sphingosine=50:45:5 mol % were dissolved in 20 ml of warm ethanol heated to about 60° C., and this ethanol solution was poured into distilled water (400 ml) for injection being stirred with heating at about 70° C. to give a suspension of liposomes having a small particle size of about 60 nm. This liposome suspension was subjected to ultrafiltration to remove ethanol, and concentrated to about 30 ml. DMDC (150 mg) was added to this liposome suspension and the mixture was freeze-dried by a conventional method. A 5 wt % aqueous glucose solution (10 ml) heated to about 70° C. was added to this freeze-dried liposome product. After rehydration, a stirring treatment gave a liposome suspension. To unify the liposome particle size of this suspension, the suspension was subjected to sizing treatment using an Extruder (manufactured by Lipex Biomembranes Inc.) equipped with a Nucleopore membrane (manufactured by Nomura Microscience) having a pore diameter of from 0.6 to 0.2 µm to give uniform liposomes having an average particle size of about 160 nm. Then, DMDC not encapsulated was removed by ultrafiltration to give DMDC liposomes.

EXAMPLE 5

DMDC in Example 1 is changed to 2'-deoxy-2'-fluoromethylidenecytidine, 2'-deoxy-2'-methylidene-5-fluorocytidine, 2'-deoxy-2',2'-difluorocytidine or 2'-C-cyano-2'-deoxy-β-arabinofuranosylcytosine and a liposome preparation is prepared in the same manner.

Control Example 1

DMDC was dissolved in a 2.5 wt % aqueous lactic acid solution to a DMDC concentration of 15 mg/ml.

Comparative Example 1

HSPC (235.5 mg) and cholesterol (116.0 mg) were dissolved in 10 ml of warm ethanol heated to 60° C. to give an ethanol solution. DMDC liposomes were obtained in the same manner thereafter as in Example 2.

Experimental Example 1

Figure 1:
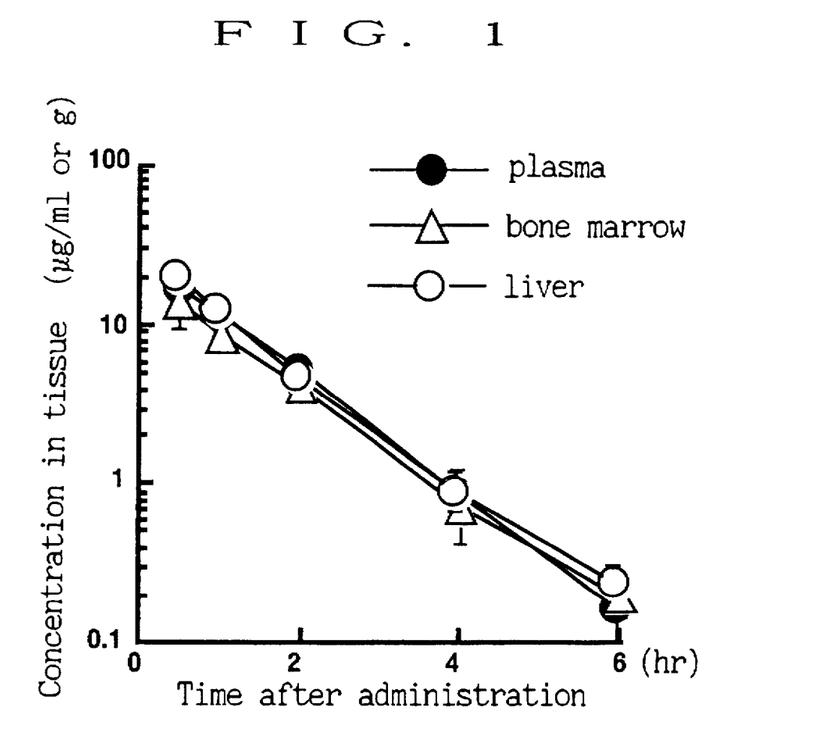
FIG. 1 shows the results of Experimental Example 1.

The DMDC solution obtained in Control Example 1 was intravenously administered to a group of three to eight male SD rats at 30 mg/kg of DMDC. After administration, plasma, liver and bone marrow were taken at 0.25, 0.5, 1, 2, 4 and 6 hours with the passage of time, and DMDC concentration was determined. Migration to organ was evaluated from Kp value (concentration in tissue/ concentration in plasma) which shows a ratio of concentration in tissues of liver and bone marrow to concentration in plasma. Quantitative determination was performed by HPLC wherein the limit of determination was 0.1 µg/ml (plasma), 0.5 µg/ml (liver) and about 0.25 ng/g (bone marrow). As a result, the level of concentration in bone marrow or liver of the rats which underwent intravenous injection of the aqueous solution was almost the same as that in plasma, as shown in FIG. 1. The Kp value was about 1.2 in liver and 0.9 in bone marrow, and almost the same at each determination.

Experimental Example 2

Figure 2:
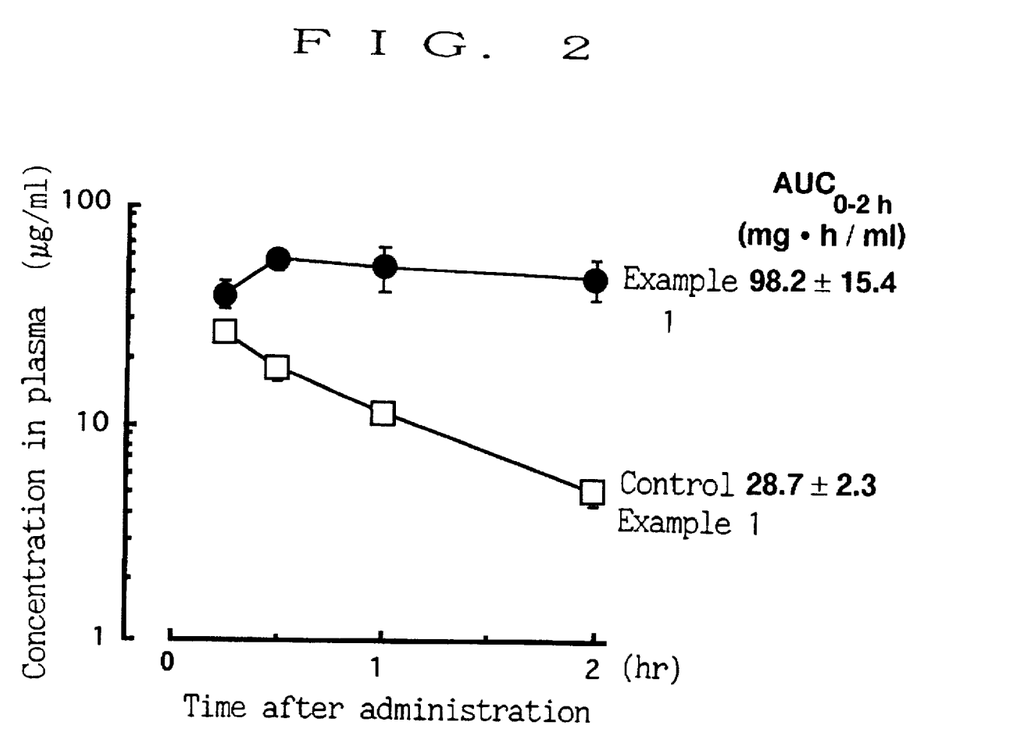
FIG. 2 shows the results of Experimental Example 2.

The DMDC liposome preparation obtained in Example 1 and the DMDC solution obtained in Control Example 1 were intravenously administered to the groups of three to eight male SD rats at 30 mg/kg of DMDC. After administration, plasma was taken at 0.25, 0.5, 1 and 2 hours with the passage of time, and liver and bone marrow were taken at the end of the test, which was followed by determination of DMDC concentration. Migration to organ was evaluated from Kp value (concentration in tissue/concentration in plasma) which shows a ratio of concentration in tissue to concentration in plasma. As a result, when compared to the control group, the concentration in plasma was noticeably maintained and AUC (area under curve) at 2 hours later was about 3.4 times greater, as shown in FIG. 2. As shown in Table 1, migration to liver or bone marrow decreased to about ½.

TABLE 1

|  | Concentration in plasma (μg/ml) | Concentration in liver (μg/g) | Concentration in bone marrow (μg/g) |
| --- | --- | --- | --- |
| Control | 5.1 ± 1.1 | 4.7 ± 1.0 | 4.0 ± 0.8 |
| Example 1 | (1) | (0.9 ± 0.1) | (0.8 ± 0.2) |
| Example 1 | 38.1 ± 5.3 | 22.5 ± 3.2 | 12.4 ± 1.2 |
|  | (1) | (0.6 ± 0.2) | (0.3 ± 0.1) |

Note: The numerals in parentheses show Kp value (concentration in tissue/concentration in plasma).

Experimental Example 3

Figure 3:
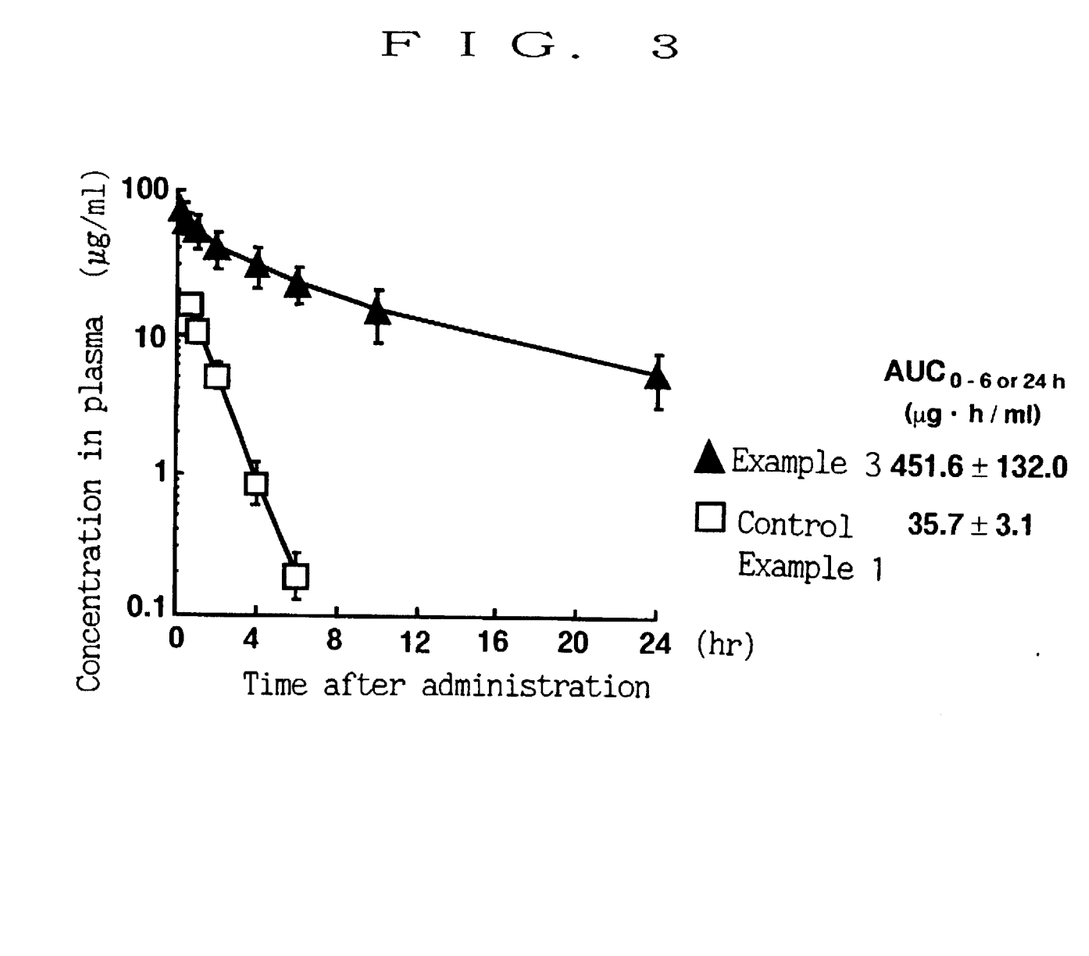
FIG. 3 shows the results of Experimental Example 3.

The DMDC liposome preparation obtained in Example 3 and the DHDC solution obtained in Control Example 1 were intravenously administered to the groups of three to eight male SD rats at 30 mg/kg of DMDC. After administration, plasma was taken at 0.25, 0.5, 1, 2, 4, 6, 10 and 24 hours with the passage of time, and liver and bone marrow were taken at the end of the test, which was followed by determination of DMDC concentration. Migration to organ was evaluated from Kp value (concentration in tissue/ concentration in plasma) which shows a ratio of concentration in tissue to concentration in plasma. As a result, the concentration in plasma was maintained, and AUC at 2, 10 and 24 hours later was about 3 times, 8 times and 13 times greater, respectively, than the control group, as shown in FIG. 3. As shown in Table 2, migration to bone marrow decreased to about ½–about ¼ by formulation into liposomes, as evidenced by the comparison of the values at 2, 10 and 24 hours later.

TABLE 2

|  | Concentration in plasma (μg/ml) | Concentration in liver (μg/g) | Concentration in bone marrow (μg/g) |
| --- | --- | --- | --- |
| Control | 5.1 ± 1.1 | 4.7 ± 1.0 | 4.0 ± 0.8 |
| Example 1 | (1) | (0.9 ± 0.1) | (0.8 ± 0.2) |
| (at 2 hr) |  |  |  |
| Example 3 | 39.7 ± 12.0 | 22.0 ± 1.8 | 11.5 ± 3.7 |
| (at 2 hr) | (1) | (0.7 ± 0.1) | (0.4 ± 0.1) |
| Example 3 | 15.0 ± 6.1 | 7.6 ± 2.2 | 3.9 ± 1.1 |
| (at 10 hr) | (1) | (0.5 ± 0.2) | (0.2 ± 0.1) |
| Example 3 | 5.4 ± 2.3 | 6.0 ± 2.6 | 1.3 ± 0.4 |
| (at 24 hr) | (1) | (1.4 ± 1.0) | (0.3 ± 0.1) |

Note: The numerals in parentheses show Kp value (concentration in tissue/concentration in plasma).

Experimental Example 4

Figure 4:
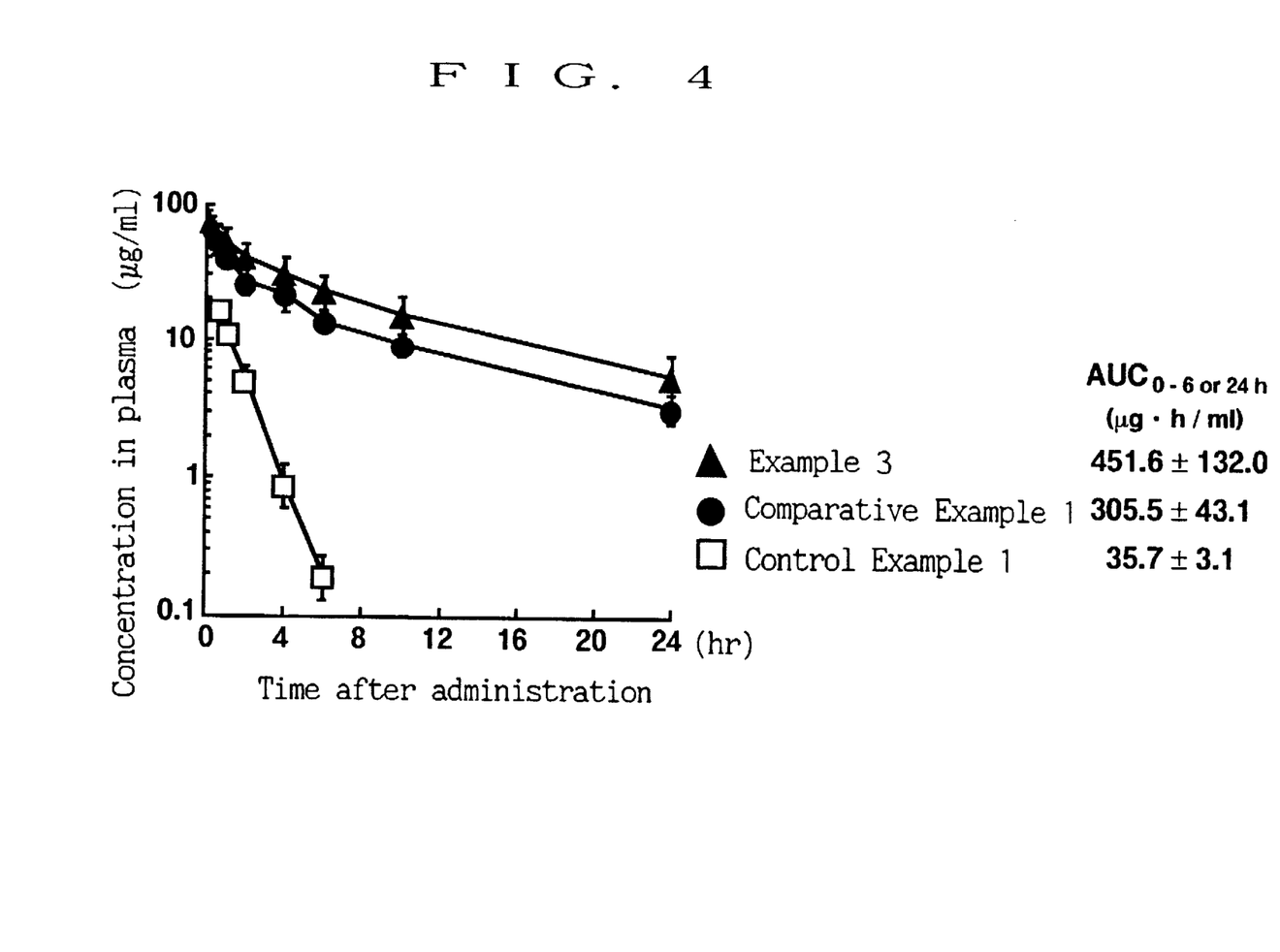
FIG. 4 shows the results of Experimental Example 4.

The DMDC liposome preparations obtained in Example 3 and Comparative Example 1 and the DMDC solution obtained in Control Example 1 were intravenously administered to the groups of three to eight male SD rats at 30 mg/kg of DMDC. After administration, plasma was taken at 0.25, 0.5, 1, 2, 4, 6, 10 and 24 hours with the passage of time, and liver and bone marrow were taken at the end of the test, which was followed by determination of DMDC concentration. Migration to organ was evaluated from Kp value (concentration in tissue/concentration in plasma) which shows a ratio of concentration in tissue to concentration in plasma. As a result, the residence in plasma of liposome preparation of Comparative Example 1 without stearylamine decreased and AUC value also decreased, as shown in FIG. 4. The liposome preparation of Example 3 containing stearylamine showed about 1.5 times greater suppressive effect on migration to myeloid tissue than did the liposome preparation of Comparative Example 1.

TABLE 3

|  | Concentration in plasma (μg/ml) | Concentration in liver (μg/g) | Concentration in bone marrow (μg/g) |
| --- | --- | --- | --- |
| Control | 5.1 ± 1.1 | 4.7 ± 1.0 | 4.0 ± 0.8 |
| Example 1 | (1) | (0.9 ± 0.1) | (0.8 ± 0.2) |
| (at 2 hr) |  |  |  |
| Example 3 | 29.7 ± 1.7 | 22.0 ± 1.8 | 11.5 ± 3.7 |
| (at 2 hr) | (1) | (0.7 ± 0.1) | (0.4 ± 0.1) |
| Example 3 | 17.1 ± 2.6 | 7.6 ± 2.2 | 3.9 ± 1.1 |
| (at 10 hr) | (1) | (0.5 ± 0.2) | (0.2 ± 0.1) |
| Example 3 | 5.4 ± 2.3 | 6.0 ± 2.6 | 1.3 ± 0.4 |
| (at 24 hr) | (1) | (1.4 ± 1.0) | (0.3 ± 0.1) |
| Comparative | 14.3 ± 0.1 | 7.9 ± 1.1 | 8.0 ± 0.9 |
| Example 1 | (1) | (0.6 ± 0.1) | (0.6 ± 0.1) |
| (at 2 hr) |  |  |  |
| Comparative | 10.0 ± 1.0 | 9.2 ± 1.6 | 3.1 ± 1.1 |
| Example 1 | (1) | (0.9 ± 0.3) | (0.3 ± 0.1) |
| (at 10 hr) |  |  |  |
| Comparative | 3.3 ± 0.8 | 8.7 ± 2.9 | 1.2 ± 0.3 |
| Example 3 | (1) | (2.9 ± 1.6) | (0.4 ± 0.1) |
| (at 24 hr) |  |  |  |

Note: The numerals in parentheses show Kp value (concentration in tissue/concentration in plasma).

Experimental Example 5

The DMDC liposome preparations (equivalent to DMDC 100 mg/kg) obtained in Example 3 and Comparative Example 1 and the DMDC aqueous solution (DMDC 100 mg/kg) obtained in Control Example 1 were intravenously administered to male BALB/c-nu/nu nude mice grafted with LX-1 human lung cancer, once a day for 5 consecutive days from the tail vein (5 or 6 mice/group). After administration, longer (L) and shorter (W) diameters of the tumor were measured with the passage of time, and the tumor volume (V) was calculated from the following formula:

$$V = \tfrac{1}{2} \times L \times W^2$$

In each mouse, the relative tumor volume ($Vn/V_0$) was calculated, where Vn is the tumor volume on the measurement day (day n) and $V_0$ is the initial tumor volume at the time when the treatment was started (day 0). The mean value of $Vn/V_0$ for control group (Cn) and that for treated group (Tn) were calculated. T/C (%) was calculated from the following formula and used as an index of the treatment effect:

$$T/C\ (\%) = (Tn/Cn) \times 100$$

The period of observation was principally 4 weeks. Significant difference between Cn and Tn was determined by the U test of Mann-Whitney, the results of which are shown in FIG. 5.

Figure 5:
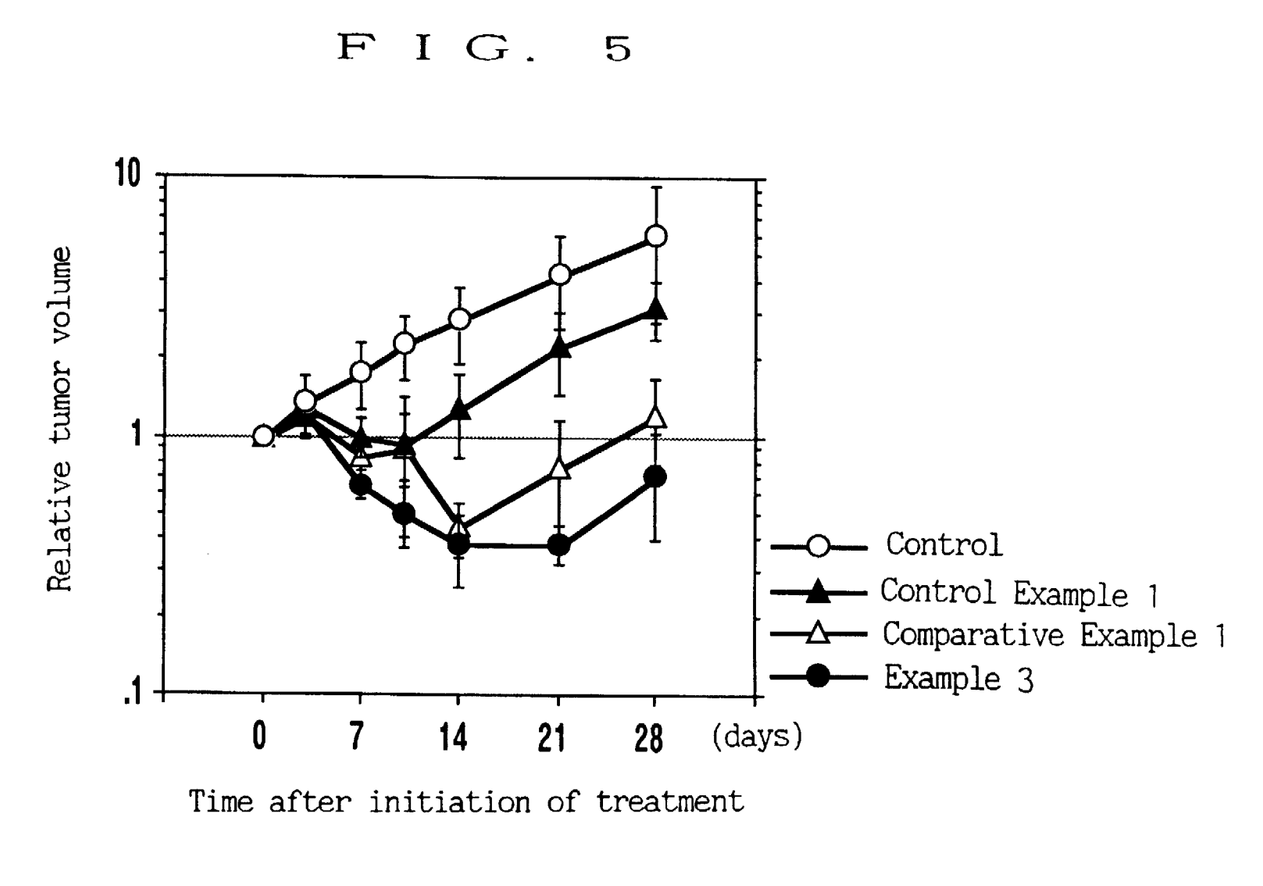
FIG. 5 shows the results of Experimental Example 5.

As is evident from FIG. 5, the DMDC liposome preparation obtained in Example 3 significantly suppressed growth of LX-1 human lung cancer. The preparation showed more markedly enhanced effects than the DMDC aqueous solution obtained in Control Example 1, and the effects were stronger than those attained by the liposome preparation of Comparative Example 1 without stearylamine. The test results suggest that the DMDC liposome preparation of the present invention shows significant treatment effects on malignant tumors.

Industrial Applicability

The liposome preparation of the present invention is not only expected to decrease toxicity to myeloid tissue, which is caused by a water-soluble 2'-deoxycytidine compound having anti-malignant tumor activity, but also expected to accumulate the active ingredient in tumor tissues by virtue of an improved residence thereof in blood. Therefore, the preparation can maintain or enhance anti-tumor effects without causing side effects, and is useful for the treatment of malignant tumors.

What is claimed is:

1. A liposome preparation which comprises (a) a liposome having an average particle size 50 to 200 nm and composed of a phospholipid selected from the group consisting of hydrogenated purified egg yolk phosphatidylcholine, hydrogenated purified soy bean phosphatidylcholine, dipalmitoylphosphatidylcholine and distearoylphosphatidylcholine, said liposome having encapsulated therein a water-soluble 2'-deoxycytidine compound, (b) 0.02–0.4 moles of stearylamine per mole of the phospholipid which positively charges the surface of the lipid membrane, and (c) 0.6–1 mole of a sterol per mole of the phospholipid as a stabilizer.

2. The liposome preparation of claim 1, wherein the 2'deoxycytidine compound is selected from the group consisting of 2'-deoxy-2'-methylidenecytidine, 2'-deoxy-2'-fluoromethylidenecytidine, 2'-deoxy-2'-methylidene-5-fluorocytidine, 2'-deoxy-2',2'-difluorocytidine and 2'-C-cyano-2'-deoxy-β-arabinofranosylcytosine, and pharmaceutically acceptable salts and hydrates thereof.

3. The liposome preparation of claim 1, wherein the 2'deoxycytidine compound is selected from the group consisting of 2'deoxy-2'-methylidenecytidine and 2'-deoxy-2'-methylidene-5fluorocytidine, and pharmaceutically acceptable salts and hydrates thereof.

4. The liposome preparation of claim 1, wherein the 2'-deoxycytidine compound is 2'-deoxy-2'-methylidenecytidine dihydrate.

5. The liposome preparation of claim 1, wherein the liposome is composed of a phospholipid selected from the group consisting of hydrogenated purified soy bean phosphatidylcholine and dipalmitoylphosphatidylcholine.

6. The liposome preparation of claim 1, wherein the liposome is composed of hydrogenated purified soy bean phosphatidylcholine.

7. The liposome preparation of claim 1, wherein the stabilizer is cholesterol.

8. The liposome preparation of claim 1, wherein the liposome has an average particle size of 100–180 nm.

9. The liposome preparation of claim 1, wherein the liposome has an average particle size of 120–160 nm.

10. The liposome preparation of claim 1, wherein the liposome has an average particle size of 150–160 nm.

11. A liposome preparation comprising a water-soluble 2'-deoxycytidine dihydrate encapsulated therein, wherein the surface of the lipid membrane is positively charged, and the liposome is composed of 0.02–0.4 mole of stearylamine or sphingosine and 0.6–1 mole of cholesterol per mole of a phospholipid selected from the group consisting of hydrogenated purified soy bean phosphatidylcholine and dipalmitoylphosphatidylcholine, and has an average particle size of 50–200 nm.

12. A liposome preparation comprising a water-soluble 2'-deoxycytidine dihydrate encapsulated therein, wherein the surface of the lipid membrane is positively charged, and the liposome consists of 0.02–0.4 mole of stearylamine and 0.6–1 mole of cholesterol per mole of a phospholipid selected from the group consisting of hydrogenated purified soy bean phosphatidylcholine and dipalmitoylphosphatidylcholine and has an average particle size of 120–160 nm.

13. The liposome preparation of claim 1, wherein the stearylamine which positively charges the surface of the lipid membrane is contained in a proportion of 0.02–0.1 per mole of the phospholipid-lipid.

* * * * *